United States Patent [19]

Mulhauser et al.

[11] Patent Number: 5,460,173
[45] Date of Patent: Oct. 24, 1995

[54] DRY POWDER INHALER MEDICAMENT CARRIER

[75] Inventors: Paul Mulhauser, New York, N.Y.; Jeffrey A. Karg, Waldwick, N.J.

[73] Assignee: Tenax Corporation, Danbury, Conn.

[21] Appl. No.: 218,031

[22] Filed: Mar. 25, 1994

Related U.S. Application Data

[63] Continuation of Ser. No. 25,964, Mar. 3, 1993, abandoned.
[51] Int. Cl.$^6$ .................. A61M 15/00; A61M 16/00; B05D 7/14; B65D 83/06
[52] U.S. Cl. .................. 128/203.15; 128/203.12; 128/204.13
[58] Field of Search .................. 128/203.15, 204.11, 128/204.12, 204.13, 202.21, 203.12, 203.23, 203.29, 203.19, 203.21–203.24

[56] References Cited

U.S. PATENT DOCUMENTS

| 480,505 | 8/1892 | Midgley et al. | 128/206.11 |
|---|---|---|---|
| 2,470,296 | 5/1949 | Fields | 128/203.15 |
| 2,470,298 | 5/1949 | Fields | 128/203.15 |
| 2,503,732 | 4/1950 | Heisterkamp | 128/203.15 |
| 2,517,482 | 8/1950 | Hall | 128/203.15 |
| 2,534,636 | 12/1950 | Stirn | 128/203.15 |
| 2,549,303 | 4/1951 | Friden | 128/203.15 |
| 2,569,720 | 10/1951 | Jesnig | 128/203.15 |

(List continued on next page.)

FOREIGN PATENT DOCUMENTS

| 0069715 | 1/1983 | European Pat. Off. | 128/203.15 |
|---|---|---|---|
| 0211595A2 | 2/1987 | European Pat. Off. | |
| 0166294B1 | 10/1989 | European Pat. Off. | |
| 0407028A2 | 1/1991 | European Pat. Off. | |
| 0424790A2 | 5/1991 | European Pat. Off. | |
| 0428380A1 | 5/1991 | European Pat. Off. | |
| 0451745A1 | 10/1991 | European Pat. Off. | |
| 0455463A1 | 11/1991 | European Pat. Off. | |
| 0467172A1 | 1/1992 | European Pat. Off. | |
| 0469814A1 | 2/1992 | European Pat. Off. | |
| 2667790 | 4/1992 | France. | |
| 2837040 | 2/1980 | Germany. | |
| 3607187A1 | 9/1987 | Germany. | |
| 4020571A1 | 6/1990 | Germany. | |
| 4004904A1 | 9/1990 | Germany. | |
| 1692470A1 | 11/1991 | U.S.S.R.. | |
| 2144997A | 3/1985 | United Kingdom. | |
| 2246299 | 1/1992 | United Kingdom. | |
| WO90/07351 | 7/1990 | WIPO. | |
| WO90/13328 | 11/1990 | WIPO. | |
| WO91/02597 | 3/1991 | WIPO. | |
| WO91/02558 | 3/1991 | WIPO. | |
| WO91/06334 | 5/1991 | WIPO. | |
| WO91/13646 | 9/1991 | WIPO. | |
| WO91/17784 | 11/1991 | WIPO. | |
| WO91/19524 | 12/1991 | WIPO. | |
| WO92/00115 | 1/1992 | WIPO. | |
| WO92/04068 | 3/1992 | WIPO. | |
| WO92/04067 | 3/1992 | WIPO. | |
| W092/04069 | 3/1992 | WIPO. | |
| WO92/04066 | 3/1992 | WIPO. | |
| 9205824 | 4/1992 | WIPO | 128/203.15 |

*Primary Examiner*—Kimberly L. Asher
*Attorney, Agent, or Firm*—Cummings & Lockwood

[57] ABSTRACT

A woven or non-woven screen mesh disc impregnated at spaced locations along its circumference with a dose of powdered medicament. The disc is selectively indexed so as to present the impregnated doses of medicament seriatim between a pair of holes in an upper and lower pressure plate in an inhalator. Air is forced through the holes in the pressure plates and the encapsulated screen mesh to entrain a dose of the powdered medicament, which is then inhaled through a mouthpiece, by the patient-user. Because the powdered medicament is impregnated into the screen mesh, the air impinging upon the mesh and the powdered medicament will cause the medicament to break up as it is pressed up against and passed through the mesh infrastructure to aerosol or atomize the same so that the medicament is presented in appropriate particle sizes for maximum benefit when inhaled.

11 Claims, 2 Drawing Sheets

U.S. PATENT DOCUMENTS

| | | | |
|---|---|---|---|
| 2,573,918 | 11/1951 | McCuiston | 128/203.15 |
| 4,841,964 | 6/1989 | Hurka et al. | 128/203.15 |
| 4,846,168 | 7/1989 | Abiko et al. | 128/203.15 |
| 4,884,565 | 12/1989 | Cocozza | 128/203.15 |
| 4,889,114 | 12/1989 | Kladders | 128/203.15 |
| 4,907,583 | 3/1990 | Wetterlin et al. | 128/203.15 |
| 5,388,573 | 2/1995 | Mulhauser et al. | 128/203.15 |
| 5,394,869 | 3/1995 | Covarrubias | 128/204.11 |
| 2,579,280 | 12/1951 | Trumbour et al. | 128/203.15 |
| 2,581,182 | 1/1952 | Fields | 128/203.15 |
| 2,592,369 | 4/1952 | Young et al. | 128/203.15 |
| 2,603,215 | 7/1952 | Arnow | 128/203.15 |
| 2,603,216 | 7/1952 | Taplin et al. | 128/203.15 |
| 2,604,094 | 7/1952 | Miller et al. | 128/203.15 |
| 2,642,063 | 6/1953 | Brown | 128/203.15 |
| 2,672,865 | 3/1954 | Willis | 128/203.15 |
| 2,772,935 | 11/1955 | Thompson et al. | |
| 2,946,332 | 7/1969 | Sacks | 128/203.15 |
| 2,992,645 | 7/1961 | Fowler | 128/203.15 |
| 3,518,992 | 7/1970 | Altounyan et al. | 128/203.15 |
| 3,669,113 | 6/1972 | Altounyan et al. | 128/203.15 |
| 3,795,244 | 3/1974 | Lax et al. | 128/203.15 |
| 3,807,400 | 4/1974 | Cocozza | 128/203.15 |
| 3,809,084 | 5/1974 | Hansen . | |
| 3,837,341 | 9/1974 | Bell | 128/203.15 |
| 3,858,583 | 1/1975 | Halworth | 128/203.15 |
| 3,870,046 | 3/1975 | Elliott | 128/203.15 |
| 3,888,253 | 6/1975 | Watt et al. | 128/203.15 |
| 3,897,779 | 8/1975 | Hansen | 128/203.15 |
| 3,906,950 | 9/1975 | Cocozza | 128/203.15 |
| 3,921,637 | 11/1975 | Bennie et al. | 128/203.15 |
| 3,948,264 | 4/1976 | Wilke et al. | 128/203.15 |
| 3,949,751 | 4/1976 | Birch et al. | 128/203.15 |
| 3,964,483 | 6/1976 | Mathes | 128/203.15 |
| 3,971,377 | 7/1976 | Damani . | |
| 3,973,566 | 8/1976 | Mathes | 128/203.15 |
| 3,980,074 | 9/1976 | Watt et al. | 128/203.15 |
| 3,991,761 | 11/1976 | Cocozza | 128/203.15 |
| 4,013,075 | 3/1977 | Cocozza | 128/203.15 |
| 4,014,336 | 3/1977 | Mathes | 128/203.15 |
| 4,047,525 | 9/1977 | Kulessa | 128/203.15 |
| 4,064,878 | 12/1977 | Lundquist | 128/203.15 |
| 4,069,819 | 1/1978 | Valentini et al. | 128/203.15 |
| 4,098,273 | 7/1978 | Glenn | 128/203.15 |
| 4,105,027 | 8/1978 | Lundquist | 128/203.15 |
| 4,116,195 | 9/1978 | James | 604/244 |
| 4,117,844 | 10/1978 | James | 128/203.15 |
| 4,147,166 | 4/1979 | Hansen | 128/203.15 |
| 4,192,309 | 3/1980 | Poulsen | 128/203.15 |
| 4,200,099 | 4/1980 | Guenzel et al. | 128/203.15 |
| 4,206,758 | 6/1980 | Hallworth et al. | 128/203.15 |
| 4,227,522 | 10/1980 | Carris | 128/203.15 |
| 4,249,526 | 2/1981 | Dean et al. | 128/203.15 |
| 4,307,734 | 12/1981 | Blankenship | 131/329 |
| 4,338,931 | 7/1982 | Cavazza | 128/203.15 |
| 4,353,365 | 10/1982 | Halworth | 128/203.15 |
| 4,371,101 | 2/1983 | Cane et al. | 222/636 |
| 4,423,724 | 1/1984 | Young | 128/203.15 |
| 4,446,862 | 5/1984 | Baum et al. | 128/203.15 |
| 4,534,345 | 8/1985 | Wetterlin | 128/203.15 |
| 4,570,630 | 2/1986 | Elliott et al. | 128/203.15 |
| 4,620,847 | 11/1986 | Shishov et al. | 604/58 |
| 4,627,432 | 12/1986 | Newell et al. | 128/203.15 |
| 4,662,915 | 5/1987 | Shirai et al. | 55/511 |
| 4,667,668 | 5/1987 | Wetterlin | 128/203.15 |
| 4,668,218 | 5/1987 | Virtanen | 604/58 |
| 4,709,837 | 12/1987 | Erdman | 222/636 |
| 4,739,754 | 4/1988 | Shaner | 128/203.15 |
| 4,805,811 | 2/1989 | Wetterlin | 222/337 |
| 4,811,731 | 3/1989 | Newell et al. | 128/203.15 |

DRY POWDER INHALER MEDICAMENT CARRIER

This application is a continuation of application Ser. No. 08/025,964, filed Mar. 3, 1993, now abandoned.

BACKGROUND OF THE INVENTION

1. Field of the Invention

This invention relates to a medicament carrying disc, and more particularly, to a disc containing a dry powder medicament adapted to be housed within an inhalator usable by asthmatics and the like. By inhaling on a mouthpiece, a prescribed dosage of the medicament is entrained in an air stream and inhaled by the user through the mouthpiece to coat the lungs of the user.

2. Description of the Prior Art

Asthma and other respiratory diseases have long been treated by the inhalation of an appropriate medicament to coat the bronchial tubes in the lungs to ease breathing and increase air capacity. For many years the two most widely used and convenient choices of treatment have been the inhalation of a medicament from a drug solution or suspension in a metered dose aerosol, pressurized inhalator, or inhalation of a powdered drug generally admixed with an excipient, from a dry powder inhalator. With growing concern being voiced over the strong link between depletion of the earth's atmospheric ozone layer and clorofluorocarbon emissions, use of these materials in pressurized inhalators is being questioned, while an interest in dry powder inhalation systems has accordingly been stimulated.

Small quantities of a fine particle, preferably micronized powder, are used mainly for therapeutic purposes in treating diseases of the respiratory tract. Powders of this type, such as salmeterol hydronapthoate, in quantities generally below 50 micrograms (μg) are added to the respiratory air of the lung of the patient. It has been found that the particles of active materials should have a particle size of less than 5 microns (μ) in thickness to insure that they penetrate deep into the lung. Thus, the metered dose must be atomized, aerosolized, or sufficiently broken up for inhalation by the patient to achieve the desired effect in the required dosage.

Presently, there are four different principal methods in use to provide fine particle powders without the use of propellants in the treatment of diseases of the respiratory tract.

The first method relies on the use of hard gelatin capsules which contain both a dose of the active material, and, in addition, potential adjuvants. The inhalator used by the asthmatic patient comprises a device for perforating or opening the capsule which is inserted into the inhalator when required. An air stream generated by a vacuum created by sucking action by the patient on a mouthpiece of the inhalator removes the powder contained within the opened capsule. The empty capsule is then expelled from the inhalator, which is then ready to receive the next capsule. Inhalators using this capsule-perforating technology or capsule-opening technology are shown in U.S. Pat. Nos. 3,906,950; 4,013,075; 3,807,400; and 3,991,761. In these inhalators, the capsule, when perforated, has both its ends held still during inhalation. The air stream which passes through it as a result of inhalation removes the powdered medicaments and is intended to remove all of the powdered medicament from the interior of the opened or broken capsule. However, it has been found that the air stream induced by the user-patient is generally insufficient in duration to remove the entire contents from the capsule which acts as a housing and in fact, impedes the removal of the medicament.

A further type of inhalator does not use individual capsules but instead is loaded with a package having a series of blisters equidistant from each other adjacent to its periphery. Each blister contains a fixed quantity of powdered medicament. As shown in EPO patent application publications EPO 211595 and 455463 along with EPO 467172 A1, when each blister is moved into a predetermined position, the blister is broken by a suitable opening device releasing the powder, which is then inhaled by the patient. It has been found that small water droplets of moisture contained within the depressions in the blister pack may cause agglomeration of the prepared medicament. Accordingly, when entrained in the air stream and inhaled by the user, the preferred particle size which can do the most good may not be readily achieved.

Another type of inhalator uses a container housing a quantity of medicament sufficient for several doses and is commonly known as the Draco TURBUHALER inhalator and is described in detail in U.S. Pat. Nos. 4,668,218, 4,667,668 and 4,805,811. The container includes a device for withdrawing the powdered medicament from the container and for preparing a dose for inhalation. The withdrawal and dose preparation includes a plate having a predetermined thickness and a certain number of cup-shaped or frusto-conical through holes. The plate can be moved by mechanical means from a position where a proportion of the holes are filled with powdered medicament taken from the container to another position in which the holes filled with medicament are located within a channel. Air flows into the channel as a result of suction provided by the patient on a mouthpiece in communication with the channel, to remove the powdered medicament from the holes. A scraper device is provided to level the powder in the plate holes and insures complete filling of the holes and consequently a constant dose. It has been found however that when suction is applied to entrain the medicament from one or more holes in the plate, not all the medicament is entrained but due to insufficient breathing capacity of the user and the non-cylindrical shape of the holes, some falls back into or never leaves the holes. Additionally, there is an agglomeration problem as mentioned previously. Accordingly, a vortex device has to be provided to aerosolize or atomize the agglomerated entrained medicament, even assuming the proper dosage leaves the holes in the rotated plate or disc.

Finally, a process for supplying a medicament in a dry powder inhalator is disclosed in German Patent No. 4020571 A1 in which in manufacturing the aerosol, a velour or velvet-like material loaded with powder is introduced into a jet stream of air. The jet stream of air lifts the powder from the velour-like material by the Bernoulli effect, entrains the same, which is then inhaled by the user. The problem with this type of an arrangement is that the fibers themselves intermix with the medicament.

The present invention avoids many of the problems associated with the prior art, enabling a predetermined exact dose to be supplied through an inhalator with the ingested particle size of the powdered dose being formed for maximum beneficial efficiency.

SUMMARY OF THE INVENTION

In accordance with the present invention, a woven or non-woven screen mesh disc is impregnated at spaced locations along its circumference with a dose of powdered medicament, such as salmeterol hydronapthoate, which is useful in the treatment of asthma. The disc is selectively indexed so as to present the impregnated doses of medicament seriatim between a pair of holes in an upper and lower pressure plate in an inhalator. Air is forced through the holes in the pressure plates and the encapsulated screen mesh to entrain a dose of the powdered medicament, which is then inhaled through a mouthpiece, by the patient-user.

Because the powdered medicament is impregnated into the screen mesh, which could be woven, such as a silkscreen, or formed from synthetic fibers, such as polyamide, polyolefin, polyester, or even naturally modified fiber such as cellulose derivatives or even stamped or etched from a piece of metal or ceramic e.g., glass or porcelain, the air impinging upon the mesh and the powdered medicament will cause the medicament to break up as it is pressed up against and passed through the mesh infrastructure to aerosol or atomize the same so that the medicament is presented in appropriate particle sizes for maximum benefit when inhaled. Further, due to the porous nature of the mesh screen and the interstitial deposit of the medicament, turbulent air can completely surround each medicament dose and entrain it, to assure complete dispensing of the medicament dose from the mesh into the air stream. The turbulence can be created in the air flowing through the mesh by passing it through a nozzle and bottom pressure plate in such a manner to create pressure changes resulting in turbulence of the air as it passes through the mesh to assist in breaking up the compressed dose.

BRIEF DESCRIPTION OF THE DRAWINGS

Further object and advantage of the invention will become apparent from the following description and claims, and from the accompanying drawings, wherein:

DETAILED DESCRIPTION OF THE PREFERRED EMBODIMENT

Figure 1:
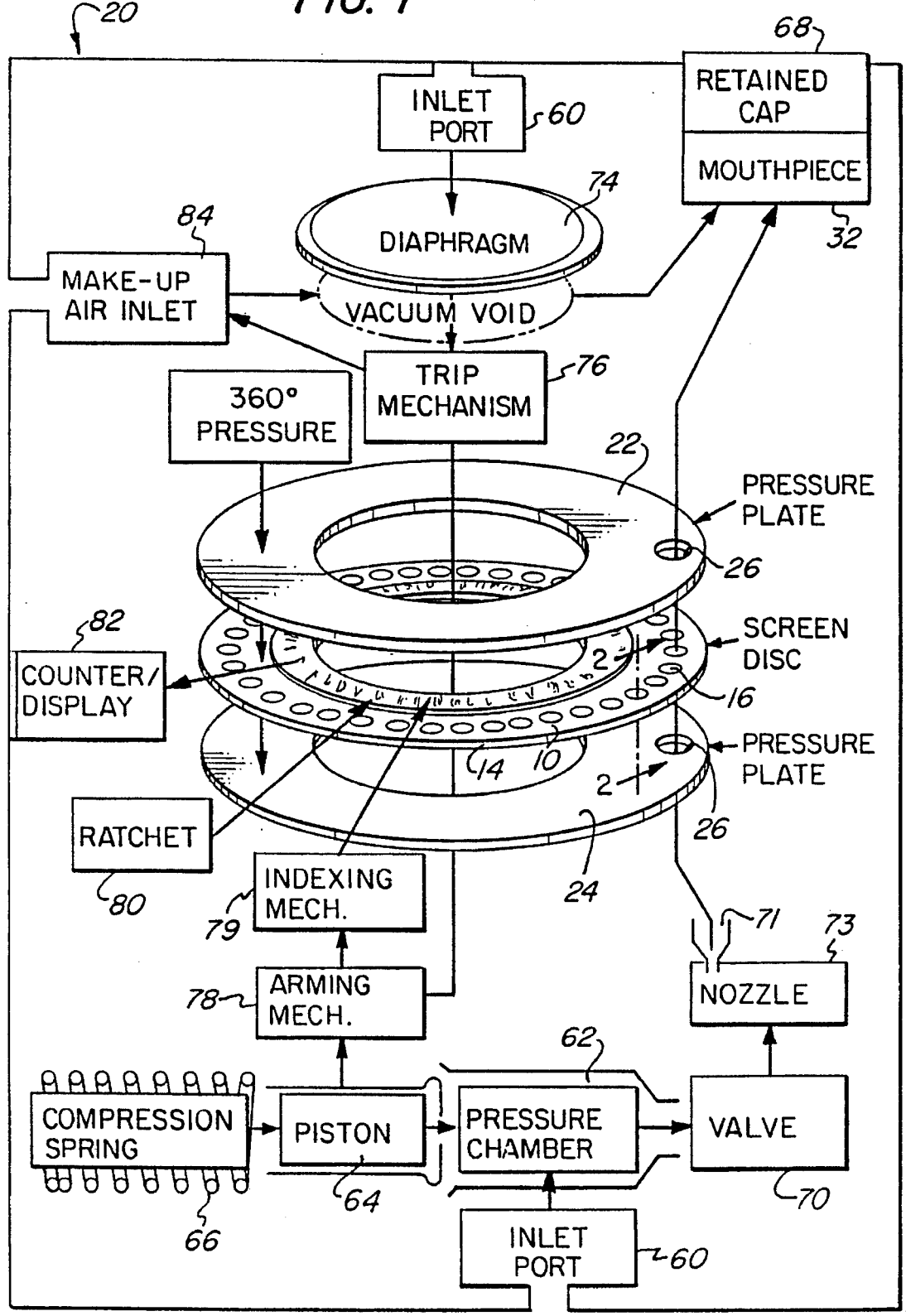
FIG. 1 is a diagrammatic view illustrating the manner of use of the dry powder medicament carrier of the present invention in an inhalator.

Referring now to the drawings in detail, wherein like numerals indicate like elements throughout the several views, a screen mesh disc 10 is illustrated in FIG. 1 which constitutes a medicament carrier forming the subject of the instant invention.

The medicament carrier 10 is of a size to be inserted within a breath-activated dry powder inhalator diagrammatically illustrated in FIG. 1 by the numeral 20.

The screen mesh disc 10 can be formed from woven or non-woven material, or stamped from a metal blank or even photo acid etched from stainless steel or ceramic to provide a plurality of small interstices 12. Compressed within the interstices 12 at spaced locations along the circumference 14 of the screen mesh disc 10 is a prescribed dose 16 of a medicament. The size of the dose 16 depends upon the drug used. For example, a common drug used for asthmatics is salmeterol hydronapthoate which is to be dispensed in single doses of approximately 50 micrograms. Each medicament dose 16 of this drug could be approximately 0.030 to 0.250 inches in diameter with a thickness of about 0.002–0.1 inches to achieve the prescribed dose.

The screen mesh disc 10 can be formed with interstices 12 of approximately 0.004 to 0.125 inches square and is positioned between a pair of pressure plates 22, 24 each having an enlarged opening 26 adapted to register with one of the medicament doses 16 upon indexing of the screen mesh disc 10, by suitable mechanical means. The pressure plates 22, 24 distribute the pressure about the periphery of the screen mesh disc 10 to maintain the medicament dose 16 in its impregnated position compressed in the screen mesh disc 10 adjacent the periphery 14. Air can then be forced through the pressure plate holes 26 and the encapsulated screen mesh disc 10 to entrain the dose 16 of the powdered medicament, as shown by arrow 30 in FIG. 2B, and the air stream with the entrained medicament is then inhaled through a mouthpiece 32 by the patient-user.

Figure 2A:
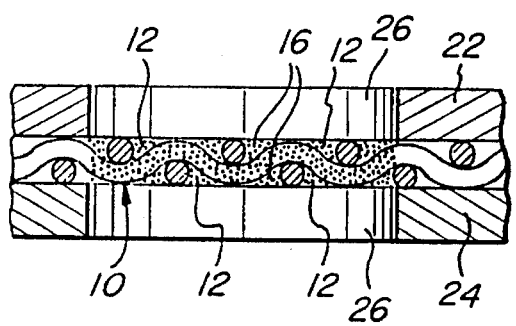
FIG. 2A is a cross-sectional view taken substantially along the plane indicated by line 2—2 of FIG. 1 and illustrates the cross-section of the medicament carrier of the present invention.
Figure 2B:
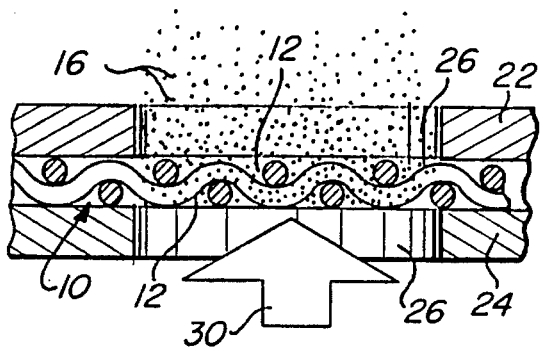
FIG. 2B is a view similar to FIG. 2A but illustrating the manner in which the medicament is entrained by air flowing through the screen mesh of the medicament carrier of the present invention.

Because the powdered medicament is impregnated and compressed into the screen mesh disc 10, which could be woven, such as a silkscreen, or formed from synthetic or natural fibers, or even stamped or etched from a piece of metal or ceramic, the air impinging upon the mesh and the powdered medicament will cause the medicament to break up as it is pressed up against and passed through the mesh infrastructure or interstices 12 between the mesh fibers or their equivalent to aerosol or atomize the same so that the medicament is presented in appropriate particle sizes for maximum benefit when inhaled. Further, due to the porous nature of the mesh screen and the interstitial deposit of the medicament, air can completely surround each medicament dose and entrain it as shown in FIG. 2B to assure complete dispensing of the medicament dose from the mesh into the air stream.

This can be contrasted with the methods used in the prior art as illustrated in FIGS. 3A to 5, inclusive.

Figure 5:
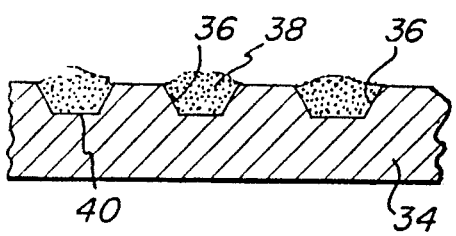
FIG. 5 is a cross-sectional view of a prior art blister-type medicament carrier utilized by prior art inhalators.

As illustrated in FIG. 5, a package 34 having a series of blisters 36 equidistant from each other adjacent to its periphery has been utilized in a dry powder inhalator. Each blister contains a fixed quantity of powdered medicament 38. When each blister 36 is moved into a predetermined position, the blister 36 is broken by a suitable opening device releasing the powder 38, which is then inhaled by the patient. It has been found that small water droplets of moisture contained within the depressions 40 in the blister 36 cause agglomeration of the prepared medicament 38. Accordingly, when entrained in the air stream and inhaled by the user, the preferred particle size which can do the most good is not readily achieved.

Figure 4A:
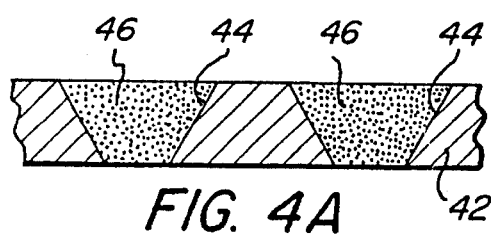
FIGS. 4A AND 4B are cross-sectional views of another solid medicament carrier disc of the prior art, with the arrows in FIG. 4B illustrating the manner in which the medicament in the disc is entrained in an inhalator air flow.
Figure 4B:
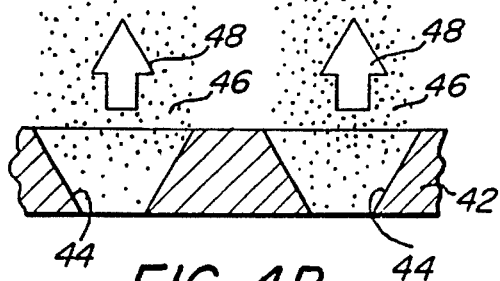

Another type of inhalator uses a container housing a quantity of medicament sufficient for several doses. The container includes a device for withdrawing the powdered medicament from the container and for preparing a dose for inhalation. The withdrawal and dose preparation includes a plate 42 as shown in FIG. 4A having a predetermined thickness and a certain number of cup-shaped or frusto-conical, through holes 44. The plate can be moved by mechanical means from a position where a proportion of the holes 44 are filled with powdered medicament 46 taken from the container to another position in which the holes filled with medicament are located within a channel. Air flows into the channel, as indicated by arrows 48 in FIG. 4B, as a result of suction provided by the patient on a mouthpiece in communication with the channel, to remove powdered medicament 46 from the holes 44. A scraper device is provided to level the powder in the plate holes 44 and insures complete filling of the holes and consequently a constant dose. It has been found however that when suction is applied to entrain the medicament from one or more holes 44 in the plate 42, not all the medicament is entrained but due to insufficient breathing capacity of the user and the non-cylindrical shape of the holes, some falls back into or never leaves the holes 44 as clearly illustrated in FIG. 4B. Additionally, there is an agglomeration problem as mentioned previously. Accordingly, a vortex device has to be provided to aerosolize or atomize the agglomerated entrained medicament, even assuming the proper dosage leaves the holes in the rotated plate 42.

Figure 3A:
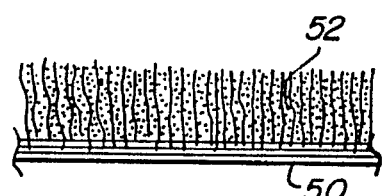
FIGS. 3A AND 3B are cross-sectional views of a prior art medicament carrier, and more particularly, one containing velour or velvet-like fibers and illustrating in FIG. 3B the manner in which the medicament embedded within the fibers is entrained within the air flow of an inhalator.
Figure 3B:
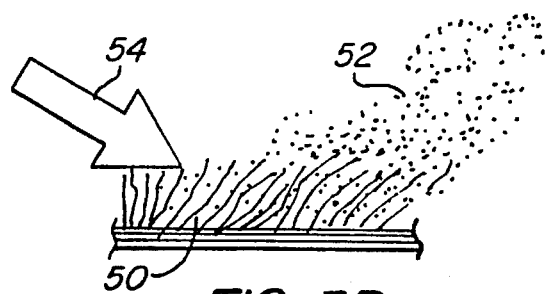

Finally, as illustrated in FIG. 3A, a velour or velvet-like material 50 loaded with medicament powder 52 is introduced into a jet stream of air, indicated by arrow 54 in FIG. 3B. The jet stream of air 54 lifts the powder 52 from the velour-like material 50 by the Bernoulli effect, entrains the same, which is then inhaled by the user. The problem with this type of an arrangement is that the fibers of the velour material 50 themselves intermix with the medicament.

In use, as illustrated in FIG. 1, the screen mesh disc 10 is clamped between pressure plates 22 and 24 with dose 16 indexed between holes 26 in the pressure plates in inhalator 20. Air used to entrain the medicament dose 16 and remove the same from screen mesh disc 10 through interstices 12 can be supplied through an inlet port 60 to a pressure chamber or cylinder 62 housing a piston 64, normally held against movement by a compression spring 66. A cap 68 can be removed from the mouthpiece 32 of inhalator 20 and a vacuum induced in the inhalator passageway 71 in a nozzle 73 to cause a valve 70 to open and communicate with the low pressure induced in the passageway 71, which in turn will enable compression spring 66 to move piston 64 into the pressure chamber 62 to drive air from chamber 62 through the valve 70 into passageway 71 and holes 26 in pressure plates 22, 24 to completely entrain the medicament dose 16 and deliver the same for inhalation through mouthpiece 32.

The screen disc 10 can then be manually indexed upon rearming of the inhalator to present another medicament dose 16 between holes 26 while the valve 70 is closed and air is introduced into pressure chamber 62 to return piston 64 to a cocked position against the force of compression spring 66.

Alternatively, air from inlet port 60 can be made to impinge upon a diaphragm 74 to activate a trip mechanism 76 upon air being withdrawn from passageway 71 through mouthpiece 32. The trip mechanism 76 can actuate an arming mechanism 78 to drive an indexing mechanism 79, for indexing the screen mesh 10, e.g., through an indexing mechanism 79 which causes a ratchet 80 to cam the screen disc 10, permitting disc 10 to rotate the predetermined distance between doses 16. A counter display 82 can display the number of doses 16 remaining on the screen mesh disc 10. Air from a make-up air inlet 84 can return the diaphragm 74 to its inactivate position.

What is claimed is:

1. A medicament carrier for use in a dry powder breath-activated inhalator apparatus having peripheral portion, including a plurality of interstices, a plurality of discrete predetermined doses of a powdered medicament embedded in only said peripheral portion of said carrier in said interstices at spaced locations along said peripheral portion, each of said discrete predetermined doses being embedded across and spanning the space between a plurality of said interstices in said peripheral portion of said carrier for entrainment with a flow of air introduced through said portion.

2. The medicament carrier of claim 1 wherein said carrier is formed from silkscreen.

3. The medicament carrier of claim 1 wherein said carrier is formed from metal.

4. The medicament carrier of claim 1 wherein said carrier is formed from ceramic material.

5. The medicament carrier of claim 1 wherein said carrier is formed from woven fibers.

6. The medicament carrier of claim 1 wherein said carrier is formed from non-woven fibers.

7. The medicament carrier of claim 1 wherein said interstices have a uniform cross-section throughout the depth of the carrier.

8. The medicament carrier of claim 7 wherein said interstices are generally square in plan.

9. The carrier of claim 1 wherein said interstices in said portion are larger than the space therebetween.

10. A medicament carrier for use in a dry powder breath-activated inhalator apparatus comprising at least one portion including a plurality of interstices, each of which are generally square in plan, a plurality of discrete, predetermined doses of powdered medicament embedded in the interstices of said carrier at spaced locations along the periphery thereof, and spanning the space between a plurality of said interstices for entrainment with a flow of air introduced through said one portion, and each of said predetermined doses being approximately 0.030 to 0.250 inches in diameter with a thickness of about 0.002 to 0.1 inches.

11. The medicament carrier of claim 10 wherein said interstices are approximately 0.004 to 0.125 inches square.

* * * * *